US00PP23605P3

(12) United States Plant Patent
Olesen

(10) Patent No.: US PP23,605 P3
(45) Date of Patent: May 21, 2013

(54) MINIATURE ROSE PLANT NAMED 'POULPAR066'

(50) Latin Name: *Rosa hybrida*
Varietal Denomination: Poulpar066

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 27 days.

(21) Appl. No.: 13/317,244

(22) Filed: Oct. 13, 2011

(65) Prior Publication Data

US 2013/0097750 P1 Apr. 18, 2013

(51) Int. Cl.
*A01H 5/00* (2006.01)

(52) U.S. Cl.
USPC ..... Plt./122

(58) Field of Classification Search
USPC ..... Plt./122
See application file for complete search history.

*Primary Examiner* — Kent L Bell

(57) ABSTRACT

A new miniature rose plant that has abundant, red flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa hybrida.*
Variety denomination: 'Poulpar066'.

SUMMARY OF THE INVENTION

The present invention constitutes a new and distinct variety of miniature rose plant which originated from a controlled crossing between the female seed parent, an unnamed seedling, and the male pollen parent, an unnamed seedling.

The two parents were crossed during the summer of 2006 and the resulting seeds were planted in a controlled environment in Fredensborg, Denmark. The new variety, named 'Poulpar066', originated as a single seedling from the stated cross.

The objective of the hybridization of this rose variety for commercial culture was to create a new and distinct variety with unique qualities, such as:

1. Uniform and abundant red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar066' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar066' was selected by the inventor as a single plant from the progeny of the hybridization in 2006.

Asexual reproduction of 'Poulpar066' by cuttings and traditional budding was first done by Mogens N. Olesen in the nursery in Fredensborg, Denmark in June 2007. This initial and other subsequent propagations conducted in controlled environments have demonstrated that the characteristics of 'Poulpar066' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar066'.

DETAILED DESCRIPTION OF THE VARIETY

The following is a description of 'Poulpar066', as observed in its growth in an open air field nursery in Benton County, Oreg. Observed plants are 20 months of age. Color references are made using The Royal Horticultural Society (London, England) Colour Chart, 2001, except where common terms of color are used.

For a comparison, several physical characteristics of the rose variety 'Poupar029', U.S. Plant Pat. No. 16,848. are compared to 'Poulpar066' in Chart 1.

CHART 1

| | 'Poulpar066' | 'Poupar029' |
|---|---|---|
| Petalage: | 45 petals | 30 petals |
| Flower Diameter: | 40 to 50 mm | 35 mm |
| General Tonality of Flower Color: | Red Group 46B | Red Group 53A |

FLOWER AND FLOWER BUD

Blooming habit: Continuous.
Flower bud:

*Size.*—Upon opening, 15 mm in length from base of receptacle to end of bud. 11 mm in diameter.

*Bud color*.—As sepals unfold, petals are a blend of Greyed-Purple Group 185A and Red Group 46A.

*Sepals*.—Upper Surface: Color: Greyed-Purple Group 183A and N 186C and Yellow-Green Group 146C. Texture: Smooth. Strongly Pubescent. Lower Surface: Color: Yellow Green Group 146C with strong intonations of anthocyanin the color of Greyed-Purple Group 183A. Texture: Somewhat rough with many stipitate glands. Shape: Apex: Cirrhose. Base: Flat at union with receptacle. Margins: Margins have strong and medium foliaceous appendages on three of the five sepals. Size: 25 mm long by 6 mm wide.

*Receptacle*.—Surface Texture: Smooth. Shape: Campanulate. Size: 5 mm tall by 5 mm wide. Color: Yellow-Green Group 144A. Anthocyanin: Greyed-Purple Group 183A.

*Pedicel*.—Surface: Somewhat rough with stipitate glands. Length: 25 to 30 mm. Diameter: About 2.5 mm. Color: Yellow-Green Group 144A with strong intonations of Greyed-Purple Group 183A. Strength: Strong.

*Peduncle*.—Surface: Smooth. Length: 15 to 90 mm. Diameter: 2 to 3 mm. Color: Yellow-Green Group 146C with strong intonations of Greyed-Purple Group 183A. Borne: In panicle like clusters of 5 to 11 flowers per flowering branch.

Flower bloom:

*Fragrance*.—Moderate floral, fern like scent.

*Duration*.—Flowers last from 21 to 28 days under moderate temperatures.

*Size*.—40 to 50 mm diameter when fully opened. Depth is about 20 to 25 mm.

*Form*.—Flowers are hybrid tea in shape, with a tightly closed pointed center.

*Shape of flower, side view*.—The upper portion is a flattened convex. The lower portion is concave.

Petalage: There are 45 petals, 3 to 5 of which are petaloids.

Color:

*Upon opening, petals*.—Outer and inner petals: Upper Surface: Red Group 46B. Lower Surface: Red Group 46A.

*Upon opening, basal petal spots*.—Yellow-Green Group 150D on upper and lower surfaces.

*After opening, petals*.—Outer and inner petals: Upper Surface: Red Group 46B. Lower Surface: Red Group 46A.

*After opening, basal petal spots*.—Yellow-Green Group 150D on upper and lower surfaces.

General tonality: On open flower Red Group 46B. No change in the general tonality.

Petals:

*Petal reflex*.—Very strong.

*Petal margin*.—Entire and uniform. No undulations.

*Shape*.—Broad elliptic. Base: Round. Apex: Acute and rounded.

*Size*.—On average, 28 mm in length by 30 mm wide. Inner petals are about 20 mm long by 15 mm wide.

*Thickness*.—Average.

Petaloids:

*Quantity*.—Normally, there are 3 to 5.

*Size*.—About 8 mm long by 4 mm wide.

*Shape*.—Apex is acute. Base is acute. Generally the petaloids are elliptic.

*Color*.—Petal spots are Yellow Group 7D on upper and lower surfaces. Upper is Red Group 46B. Lower is Red Group 46A.

Reproductive organs:

*Pollen*.—None observed.

*Anthers*.—Size: 2 mm long. Color: Yellow Group 8B. Quantity: Average 55.

*Filaments*.—Color: Red Group 39A. Length: 4 mm.

*Pistils*.—Length: 4 mm long. Quantity: Average 35.

*Stigmas*.—Level in relation to the length of the filaments and the height of the anthers. Color: Red Group 39D.

*Styles*.—Color: Red Group 52A.

*Seed formation*.—Not observed.

PLANT

Plant growth: Very compact, upright and well branched. Plants are 20 cm in height on average, and 20 cm wide.

Stems:

*Color*.—Young wood: Yellow-Green Group 146C with anthocyanin the color of Greyed-Red Group 183A. Older wood: Yellow-Green Group 146C.

*Internodal distance*.—25 mm on average.

*Length of stems*.—15 to 17 cm from base of plant to the flowering portion. Stems are about 4 mm in diameter.

*Surface texture*.—Young wood: Smooth. Older wood: Smooth with some larger prickles.

Prickles:

*Incidence*.—5 to 7 per 10 cm of stem.

*Size*.—Average length 3 mm.

*Color*.—Juvenile prickles are Greyed-Purple Group 184C. Mature prickles are Greyed-Orange Group 164D.

*Shape*.—Flat on upper side, and concave on the lower side.

Plant foliage: Normally 5 leaflets at the center of the branch.

*Compound leaf size*.—About 80 mm (l)×50 mm (w).

*Quantity*.—3 leaves per 10 cm of stem.

*Color*.—

*Juvenile foliage*.—Upper Leaf Surface: Yellow-Green Group 146A with Greyed-Red Group 178A and 178B at margins. Lower Leaf Surface: Yellow-Green Group 146A with Greyed-Red Group 178A and 178B general in location.

*Mature foliage*.—Upper Leaf Surface: Yellow-Green Group 147A. Lower Leaf Surface: Yellow-Green Group 147C.

Plant leaves and leaflets:

*Stipules*.—Size: About 5 mm in length. Shape: Linear, slightly broad based with outward extending apices. Margins: Finely serrated with few stipitate glands. Color: Yellow-Green Group 146A.

*Petiole*.—Length: About 15 mm. Diameter 2 mm. Color: Yellow-Green Group 147B on upper surface. Yellow-Green Group 146A underneath. Anthocyanin: Greyed-Purple Group 183A. Underneath: Numerous small prickles observed on lower surface.

*Rachis*.—Size: About 30 mm long. Color: Yellow-Green Group 147B with Greyed-Purple Group 183A on upper surface. Lower surface is Yellow-Green Group 146A. Underneath: Numerous small prickles observed on lower surface.

*Leaflet*.—Size: 30 mm in length by 20 mm wide on average. Margin: Serrate. General Shape: Elliptical. Apex Shape: Acute. Base Shape: Round. Texture:

Smooth. Arrangement: Odd pinnate. Venation: Reticulate. Leaf Gloss: Moderately glossy.

Disease resistance: Above average resistance to powdery and downy mildew, black spot, and *Botrytis* under normal growing conditions in Benton County Oreg.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpar066', substantially as illustrated and described herein, due to its abundant, red flowers, vigorous growth, compact habit, suitability for production from softwood cuttings in pots, and durable flowers and foliage that make the variety suitable for distribution in the floral industry.

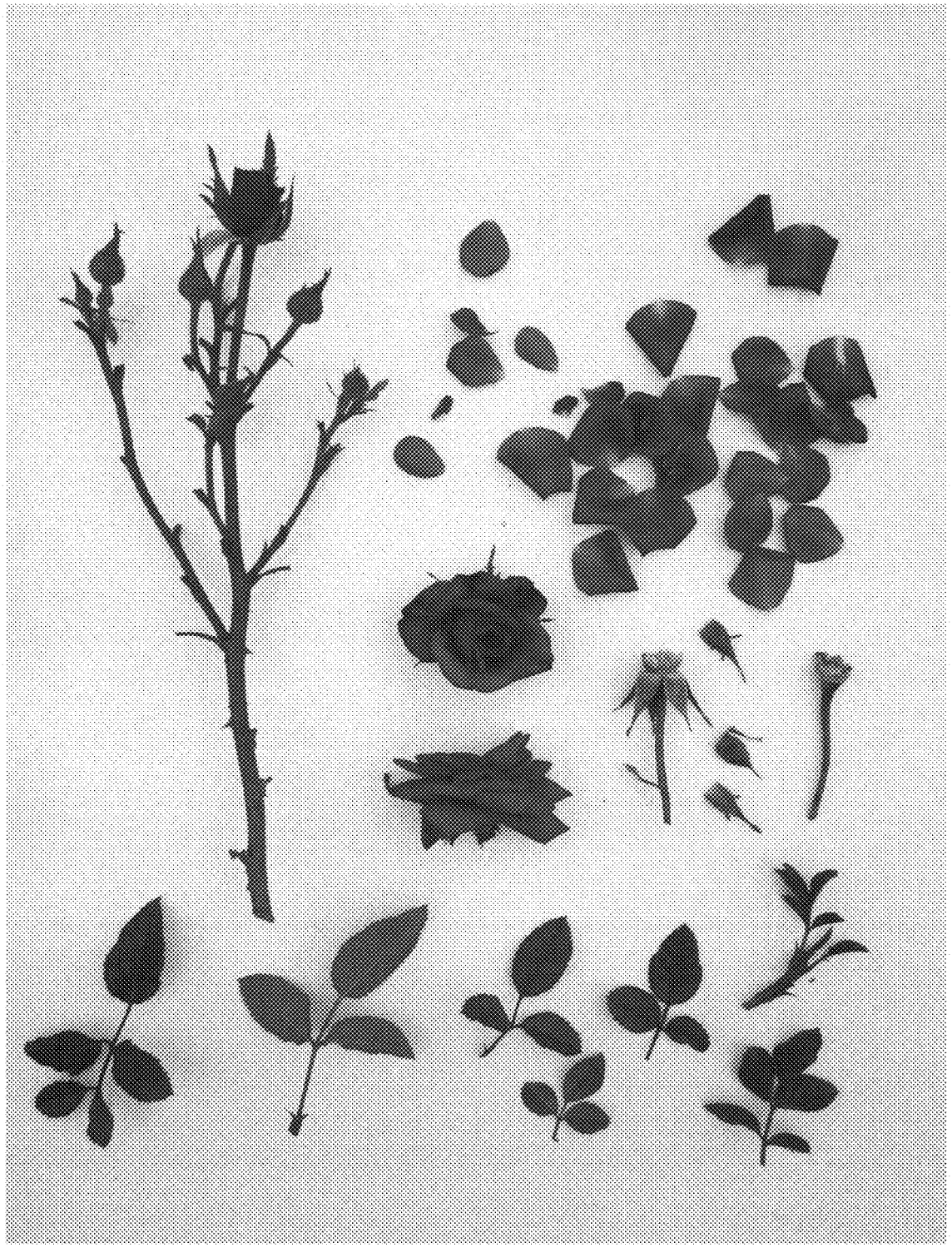

* * * * *